United States Patent [19]

Schwaninger

[11] Patent Number: 5,453,079
[45] Date of Patent: Sep. 26, 1995

[54] BLOOD FLOW VALVE FOR TREATMENT OF MALE SEXUAL IMPOTENCE

[76] Inventor: Claude L. Schwaninger, P.O. Box 33, Glenhaven, Calif. 95443

[21] Appl. No.: 260,011

[22] Filed: Jun. 15, 1994

[51] Int. Cl.[6] ............................................. A61F 2/00
[52] U.S. Cl. ............................................. 600/38
[58] Field of Search ................. 600/29, 30, 38–41; 128/831, 843, 842, 885, 886; 417/412; 137/413

[56] References Cited

U.S. PATENT DOCUMENTS

| | | | |
|---|---|---|---|
| 4,436,109 | 3/1984 | Taylor | 137/413 |
| 4,584,994 | 4/1986 | Bamberger et al. | 600/40 |
| 4,610,658 | 9/1986 | Buchwald et al. | 604/152 |
| 4,725,207 | 2/1988 | Buchwald et al. | 417/412 |
| 4,828,544 | 5/1989 | Lane et al. | 600/40 X |

Primary Examiner—Lee S. Cohen
Assistant Examiner—Samuel Gilbert
Attorney, Agent, or Firm—Larry D. Johnson

[57] ABSTRACT

A valve device which may be surgically installed in the abdomen of a user, such that the valve ports of the valve are inserted in-line with a vein returning blood from the penis to the heart, with a separate actuating magnet which may be mounted on a removable belt to be worn by the user to initiate an erection. By using a small flat magnetic plate, encapsulated in a plastic material, to form a membrane, and suspending it in front of the two valve ports, a magnetically controlled valve is formed. Placement of the remote magnet adjacent the membrane attracts the magnetic plate, closes the ports, seals the valve, and initiates the erection.

3 Claims, 2 Drawing Sheets

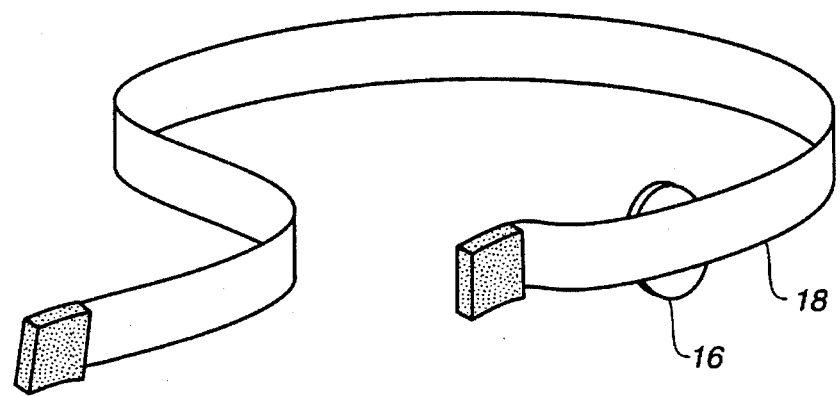
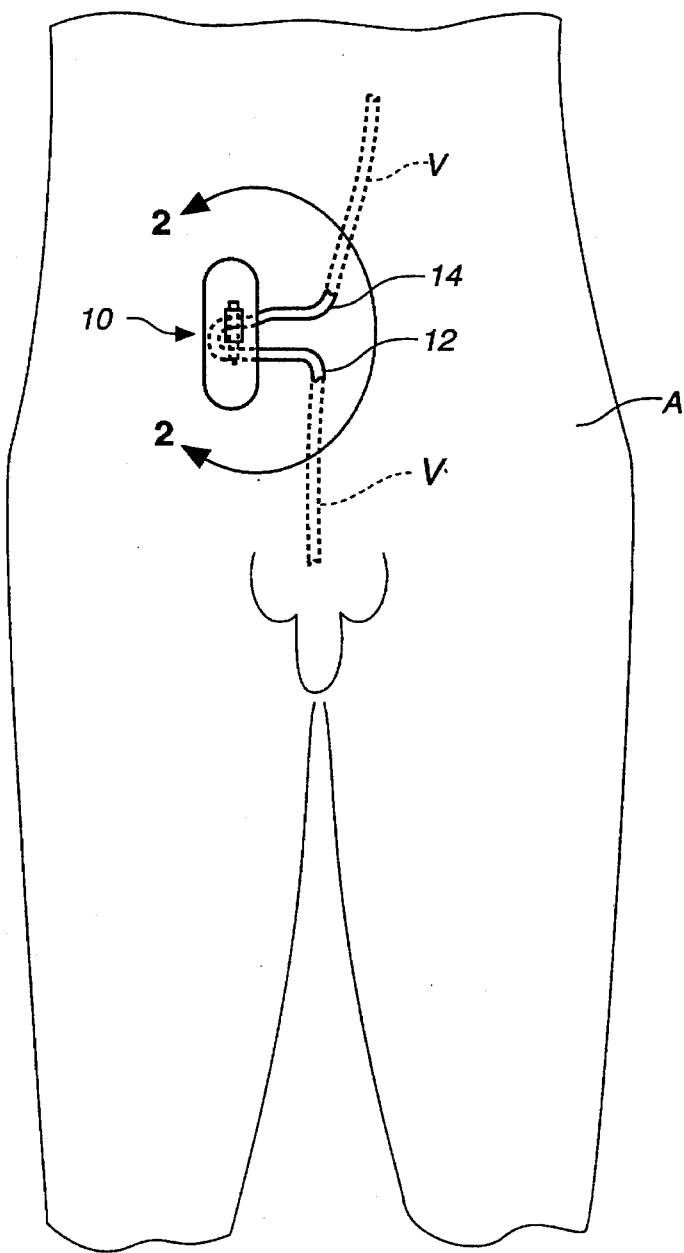
FIG._1

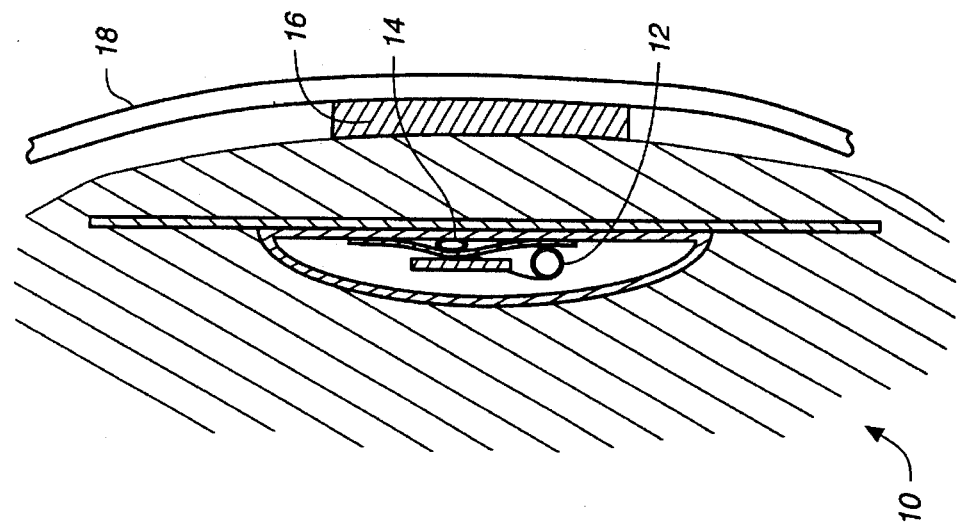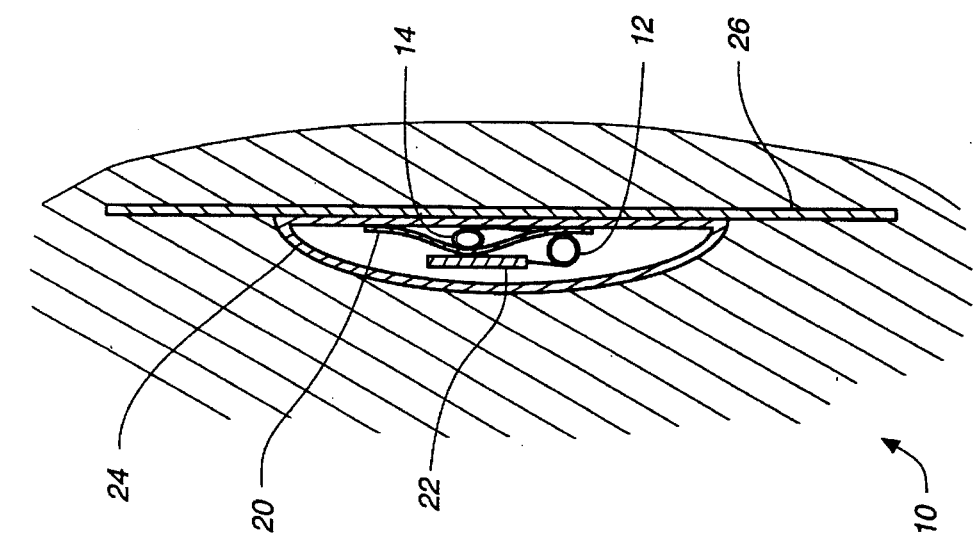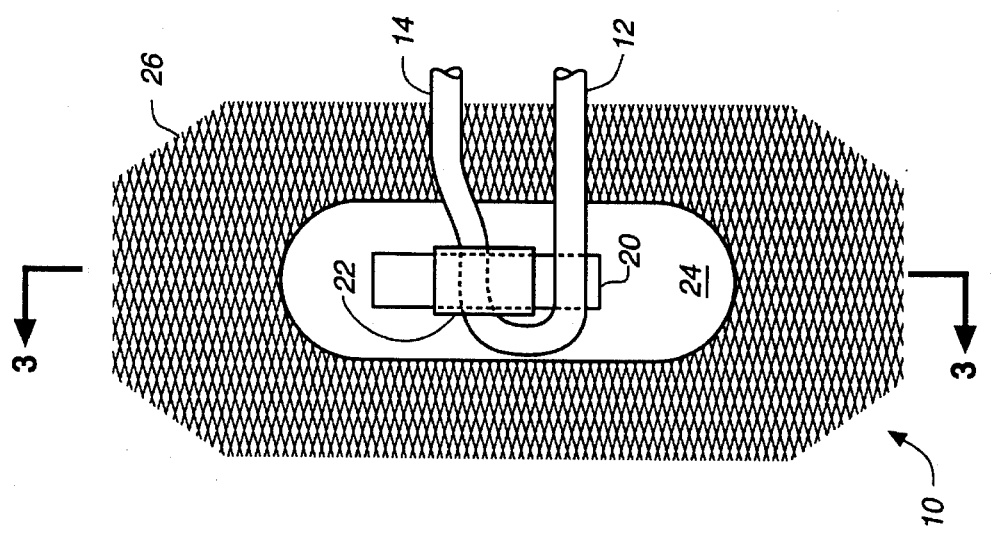

BLOOD FLOW VALVE FOR TREATMENT OF MALE SEXUAL IMPOTENCE

BACKGROUND OF THE INVENTION

1. Field of the Invention

This invention relates generally to methods and apparatus for the treatment of male sexual impotence, and more specifically to an improved remotely-actuated blood flow valve for use in such treatment.

2. Description of the Prior Art

The problem of secondary sexual impotence due to blood vessel constriction is a condition plaguing many older men, world-wide. Various ointments, salves, potions, rubber bands, and suction devices have been tried and utilized, but with only moderate success. Some vacuum pump systems have been reported to produce a good erection, but the elastic bands used to retain the system when the pump is removed compress the surface arteries and veins, as well as the urethra, much diminishing the sensory effects.

The mechanics of penile erection are believed to be as follows: under sexual arousal, release of nitric oxide into the blood causes expansion of the arteries, producing a blood surplus in the penis, and thus, an erection. Since the erection is produced by differential hydrostatic pressure between the arteries and the veins at the base of the penis, any device or substance that can produce this condition can create an erection. Various substances, such as papaverin can be injected into the penis, producing an erection, but this requires sterile procedures, syringes, hypodermic needles, etc.

It is therefore desirable to design an apparatus for the treatment of male sexual impotence that achieves the following objectives:

1. made of biologically inert materials;
2. capable of obstructing the exit of blood from the penis;
3. able to be closed at will, through at least one-half inch of skin and fat; and
4. produce a completely normal erection, on demand, without any complications or special procedures, while leading to a satisfactory sexual climax and ejaculation.

SUMMARY OF THE INVENTION

The blood flow valve for treatment of male sexual impotence of this invention provides a valve device which may be surgically installed in the abdomen of a user, such that the tubes or valve ports of the valve are inserted in-line with a vein returning blood from the penis to the heart, with a separate actuating magnet which may be mounted on a removable belt to be worn by the user to initiate an erection. By using a small flat magnetic plate, encapsulated in a plastic material, to form a membrane, and suspending it in front of the two valve ports, a magnetically controlled valve is formed. The apparatus may also include two metal ears, also of magnetic material, to concentrate the flux near the valve ports. Placement of the remote magnet adjacent the membrane attracts the magnetic plate, closing the ports, sealing the valve, and initiating the erection.

This construction has the advantage that the valve is normally open with the flow of blood tending to keep it open. In case of valve failure, it will fail in the open position, only failing to produce an erection, and not obstruct the blood flow. Otherwise, obstruction of the blood flow due to failure of the valve mechanism could cause a permanent erection, and cyanosis, with a consequent surgical emergency.

The valve is intended to be implanted in the layer of fat, just under the skin, and just below the navel, with two dacron tubes leading down to the interception point of the exit vein from the penis. A porous fabric similar to Marlex, used for hernia repair, may preferably surround the valve allowing it to be sutured in place, and to keep it from accidentally changing position.

The flat oval magnet is preferably slightly dished to fit the abdomen snugly, encircling the navel, and can be held there by an adjustable elastic belt. By using a high efficiency magnet material, such as samarium/cobalt or yttrium, the weight can be minimized, while assuring a strong enough magnetic field for reliable operation even through a layer of fat. Merely putting on the belt so that the magnet encircles the navel (and is therefore adjacent the implanted valve) will produce an erection. By using a permanent magnet field, there is no danger of deleterious effects to blood or tissue, since potential damage can occur only with AC fields.

While there are four large and two small arteries supplying blood to the penis, there are four small and only one extra-large vein draining the blood back to the heart. Thus, effectively blocking the single large vein cuts the exit capacity to one-half, which will produce an erection. In extreme cases of dysfunction, all five veins could be surgically spliced together to a common exit port. Then, with the inventive valve installed, there would be no blood at all leaving when the valve was closed, producing a vigorous erection.

BRIEF DESCRIPTION OF THE DRAWINGS

FIG. 1 is a pictorial view of the blood flow valve for treatment of male sexual impotence of this invention as surgically installed in the abdomen of a user, illustrating the tubes or valve ports of the valve inserted in-line with a vein returning blood from the penis to the heart, with an actuating magnet separately mounted on a removable belt to be worn by the user to initiate an erection;

FIG. 2 is a rear elevation view of the blood flow valve for treatment of male sexual impotence of this invention, illustrating the component parts including a valve intake tube and outlet tube, a flexible diaphragm including a magnetic valve plate, a valve housing, and surrounded by a biologically inert plastic mesh, this view taken in the vicinity of line 2—2 of FIG. 1;

FIG. 3 is a side elevation view of the blood flow valve for treatment of male sexual impotence of this invention, illustrating a diagrammatic representation of the operation of the blood flow valve, with the valve in its open (normal) configuration and permitting blood flow, this view taken in the vicinity of line 3—3 of FIG. 2; and FIG. 4 is a side elevation view of the blood flow valve for treatment of male sexual impotence of this invention, illustrating a diagrammatic representation of the operation of the blood flow valve, with the valve in its closed (erection-inducing) configuration and restricting blood flow.

DETAILED DESCRIPTION OF A PREFERRED EMBODIMENT

FIG. 1 is a pictorial view of a blood flow valve 10 for treatment of male sexual impotence of this invention as surgically installed in the abdomen A of a user, illustrating the tubes or valve ports 12, 14 of the valve inserted in-line with a vein V returning blood from the penis to the heart, with an actuating magnet 16 separately mounted on a removable belt 18 to be worn by the user to initiate an erection.

FIG. 2 is a rear elevation view of the blood flow valve 10 for treatment of male sexual impotence of this invention, illustrating the component parts including the valve intake tube 12 and outlet tube 14, a flexible diaphragm 20 including a magnetic valve plate 22, a valve housing 24, and surrounded by a biologically inert plastic mesh 26, this view taken in the vicinity of line 2—2 of FIG. 1. This is a "closed" embodiment in which the blood does not leave the valve conduit (tubes), but rather stays within the conduit, and it is the conduit itself which is captured and constricted by the magnetic plate to shut off the blood flow. An alternative embodiment could terminate one or both valve tubes in a chamber, with the magnetic valve plate being actuated to close off one or both of the valve tube openings to the chamber.

FIG. 3 is a side elevation view of the blood flow valve 10 for treatment of male sexual impotence of this invention as installed, illustrating a diagrammatic representation of the operation of the blood flow valve, with the magnetic valve plate 22 in its open (normal) configuration and therefore permitting blood flow through outlet tube 14, this view taken in the vicinity of line 3—3 of FIG. 2.

FIG. 4 is a side elevation view of the blood flow valve 10, with the magnet 16 of belt 18 having been placed adjacent the blood valve, thereby urging magnetic valve plate 22 into its closed (erection-inducing) configuration and therefore restricting blood flow through outlet tube 14. Subsequent removal of the magnet 16 will immediately return the valve to its open configuration, ending the erection.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A blood flow valve system for treatment of male sexual impotence in a male having a vein returning blood from a penis to a heart, said blood flow valve comprising:

a valve housing;

a pair of valve ports connected to the valve housing, said valve ports adapted to be inserted in-line with the vein returning blood from the penis to the heart;

a diaphragm including a magnetic element installed within said valve housing and adjacent said valve ports; and a remote actuating magnet, wherein when said remote actuating magnet is placed adjacent said diaphragm, said magnetic element closes at least one of said valve ports and restricts blood flow through the vein, thereby initiating an erection.

2. The blood flow valve system of claim 1 including a removable belt connected to said remote actuating magnet.

3. The blood flow valve system of claim 1 including a biologically inert plastic mesh connected to said valve housing.

* * * * *